(12) United States Patent
Numazawa

(10) Patent No.: US 11,364,218 B2
(45) Date of Patent: Jun. 21, 2022

(54) METHOD OF TREATING OR PREVENTING MOOD DISORDERS, MENTAL DISORDERS, AND/OR CHRONIC FATIGUE SYNDROME

(71) Applicant: Toshihiko Numazawa, Kusatsu (JP)

(72) Inventor: Toshihiko Numazawa, Kusatsu (JP)

( * ) Notice: Subject to any disclaimer, the term of this patent is extended or adjusted under 35 U.S.C. 154(b) by 1 day.

(21) Appl. No.: 17/060,079

(22) Filed: Oct. 1, 2020

(65) Prior Publication Data

US 2021/0015781 A1 Jan. 21, 2021

Related U.S. Application Data

(63) Continuation of application No. 16/315,733, filed as application No. PCT/JP2017/024871 on Jul. 6, 2017, now abandoned.

(30) Foreign Application Priority Data

Jul. 7, 2016 (JP) .............................. JP2016-134947

(51) Int. Cl.
*A61K 31/27* (2006.01)
*A61P 25/24* (2006.01)

(52) U.S. Cl.
CPC .............. *A61K 31/27* (2013.01); *A61P 25/24* (2018.01)

(58) Field of Classification Search
CPC ................................ A61K 31/27; A61P 25/24
USPC ....................................................... 514/489
See application file for complete search history.

(56) References Cited

U.S. PATENT DOCUMENTS 4,722,938 A * 2/1988 Sunshine ............... A61K 31/27
514/479

OTHER PUBLICATIONS

Bennett et al. Life sciences, 1986, 39(25, 2455-2461 (Year: 1986).*
Numazawa Open Journal of Depression, 2016, 5, 40-47 (Year: 2016).*

* cited by examiner

*Primary Examiner* — Yevgeny Valenrod
(74) *Attorney, Agent, or Firm* — Kenja IP Law PC

(57) ABSTRACT

A method of treating or preventing mood disorders, mental disorders, and/or chronic fatigue syndrome is provided. The method comprises administering to a subject in need thereof a pharmaceutical composition containing one or more kinds of compounds of the following structure:

[formula 1]

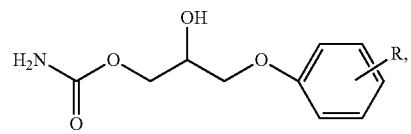

wherein R is an alkyloxy group containing 1 to 3 carbon atoms or a halogen group.

4 Claims, No Drawings

METHOD OF TREATING OR PREVENTING MOOD DISORDERS, MENTAL DISORDERS, AND/OR CHRONIC FATIGUE SYNDROME

CROSS-REFERENCE TO RELATED APPLICATIONS

This application is a continuation application of U.S. application Ser. No. 16/315,733 filed May 16, 2019, which is a National Stage Application of PCT/JP2017/024871 filed Jul. 6, 2017, which claims priority based on Japanese Patent Application No. 2016-134947 filed Jul. 7, 2016. The disclosures of the prior applications are hereby incorporated by reference herein in their entirety.

TECHNICAL FIELD

The present invention describes novel pharmaceutical compositions designed to treat mood disorders, mental disorders, and/or chronic fatigue syndrome.

BACKGROUND OF THE INVENTION

In recent years, the number of sufferers of mood and mental disorders in Japan has increased. Symptoms of depression, a type of mood disorder, have particularly increased.

The number of patients afflicted with mood disorders, including depression, was at an almost stagnant rate with 443 thousand people in 1996 and 441 thousand people in 1999, but showed a remarkable increase to 711 thousand people in 2002, 924 thousand people in 2005, and 1041 thousand people in 2008.

Many patients afflicted with mood and mental disorders exhibit a depressive state, a significant decrease in interest and joy, insomnia or oversleeping, easy fatigue, a reduction in thinking and concentration abilities, an increase or decrease in body weight, and/or repetitive suicidal thoughts. Many patients suffering from severe mood and mental disorders have difficulty maintaining a social life, and therefore, an early and reliable treatment method is desired.

In recent years, mood and mental disorders such as depression have been attributed mainly to a "lack of serotonin in the brain," and are considered "brain diseases." Thus, when attempting to treat these diseases with medication, a selective serotonin reuptake inhibitor (SSRI) is used as the main therapeutic agent. SSRIs prevent the decrease of serotonin concentrations in synapses by binding to serotonin transporters and inhibiting their reuptake of serotonin. Patent document 1 is an example of a document disclosing the SSRI.

Patent document 1: Japanese patent application laid-open no. 2004-217650

SCOPE OF THE INVENTION

Problems to be Solved by the Invention

However, when treating mood and mental disorders with SSRIs, the variation in effects due to individual patient differences is severe. In many remarkable cases no effect is observed at all. Side effects of SSRIs include increases or decreases in weight, decreases in appetite, and decreases in sexual desire. Furthermore, leaving symptoms such as dizziness, headaches, or similar effects may occur after the administration of the SSRI is complete. Thus, a reliable and safe therapeutic agent that does not rely solely on SSRI mechanisms is strongly required.

Means for Solving the Problem

As a result of intensive studies by the present investigators, a cause of these diseases different from an insufficiency of serotonin was identified, a pharmaceutical composition for ameliorating this cause was identified, and the present invention was produced.

In other words, the present invention is comprised of [1] one, two, or more kinds of compounds having the following structure, resulting in pharmaceutical compositions for treating mood disorders, mental disorders, and/or chronic fatigue syndrome:

[formula 1]

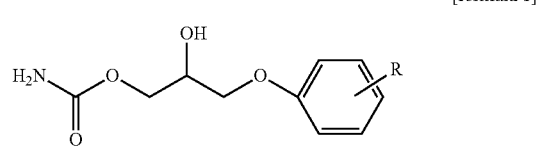

(In the formula, R is an alkyloxy group containing 1 to 3 carbon atoms or a halogen group) [2] The pharmaceutical composition according to [1], wherein R is a methoxy group or a chloro group, [3] the compound is chlorphenesin carbamate and/or methocarbamol, the pharmaceutical composition according to [1] or [2], and [4] includes chlorphenesin carbamate and methocarbamol, relating to the pharmaceutical composition according to [1] through [3].

Effects of the Invention

The pharmaceutical compositions of the present invention do not increase or decrease body weight, suggesting the possibility to provide a therapeutic agent for mood and mental disorders that does not result in adverse effects, such as decreases in appetite and/or sexual desire.

The pharmaceutical composition also functions as a therapeutic agent for chronic fatigue syndrome.

Furthermore, the pharmaceutical compositions of the present invention and other pharmaceutical compositions, including SSRIs and the like, may be combined to provide a more reliable mood and mental disorder treatment method that corresponds to the patient's symptoms.

Means for Carrying Out the Invention

The pharmaceutical compositions of the present invention may be combined with a carrier suitable for the formulation mixed with the compounds described below or any other optional components, and then obtained to be formulated.

Compound

The pharmaceutical composition comprises one or more compounds of the following structure:

[formula 2]

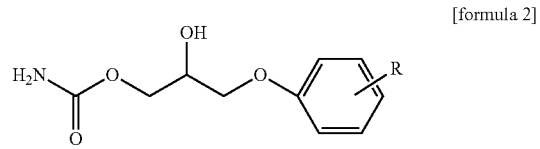

(In the formula, R is an alkyloxy group containing 1 to 3 carbon atoms or a halogen group)

The potential alkyloxy groups containing 1 to 3 carbon atoms represented by R include a methoxy group, an ethoxy group, a propyloxy group, or other similar groups. An alkyloxy group is preferred over a methoxy group.

The potential halogen groups represented by R include a chloro group, fluoro group, bromo group, or iodo group. The preferred halogen group is a chloro group.

The binding site of R is not particularly limited, and a carbon atom on a phenyl group forming an ether bond is used as a reference in either an ortho-position, a meta-position, or a para-position. When R is an alkyloxy group, it is preferred that R is located at the ortho-position. When R is a halogen group, it is preferred that R is located at the para-position A single compound of the described structure may be used alone, or two or more kinds of compounds having different structures within the range of the above structure may be used in combination.

Among the compounds mentioned above, the present pharmaceutical composition preferably includes chlorphenesin carbamate and/or methocarbamol.

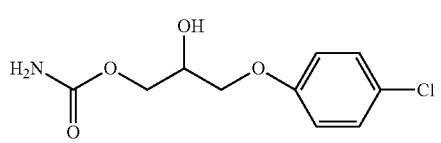

[formula 3]

(Chlorphenesin Carbamate)

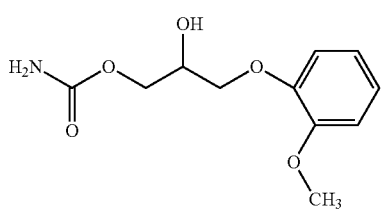

[formula 4]

(Methocarbamol)

The above compound in the present pharmaceutical composition may be used as a composite item or a commercially available product.

The present pharmaceutical composition may contain only chlorphenesin carbamate or methocarbamol as a single compound.

The present pharmaceutical composition may also include both chlorphenesin carbamate and methocarbamol.

In the case of a pharmaceutical composition comprised of both compounds, the degree of the therapeutic effect on the disease and onset of action can be adjusted.

The inventors of the present invention propose that the cause of mood disorders, mental disorders, and/or chronic fatigue syndrome is not limited to the reduction of the serotonin. Instead, the cause is a combination of several complex factors.

One of the causes of mood disorders, mental disorders, and/or chronic fatigue syndrome identified by the authors is an abnormality in surrounding tissue, such as the muscle of the inner and outer circumscribing surface of the skull.

In this case, the brain's meninges, craniofacial muscle, anterior head muscle, posterior head muscle, side head muscle, hat fascia, and chewing muscle, etc. cause abnormal tension, contraction, or fixation.

Mood disorders, mental disorders, and/or chronic fatigue syndrome arise as a result. For example, main symptoms of depression such as cessation of desire, headache, fatigue, and head fastening may occur due to abnormalities in these tissue.

Administration of the compounds described in the pharmaceutical composition above may ameliorate the symptoms of mood disorders, mental disorders, and/or chronic fatigue syndrome by relaxing these muscles of the inner or outer circumscribing surface of the skull and relaxing abnormal tension, contraction, or fixation.

If administered in advance, this pharmaceutical composition can maintain the muscle of the inner circumscribing face of the skull in a relaxed state. Furthermore, it may prevent the occurrence of mood disorder, mental disorder, and/or chronic fatigue syndrome.

A benefit of the above compound included in this pharmaceutical composition is the degree of dependency and side effects is lower than that of an SSRI.

Thus, a pharmaceutical composition of an amount sufficient to treat mood disorder, mental disorder, and/or chronic fatigue syndrome can be provided for a treatment period.

Furthermore, the present pharmaceutical composition may eliminate or prevent stress generated by stiffness of the muscle of the inner circumscribing surface of the skull.

As described above, mood disorders, mental disorders, and/or chronic fatigue syndrome are diseases that may be attributed to multiple causes. To treat mood disorders, mental disorders, and/or chronic fatigue syndrome, it is preferable to prepare a pharmaceutical composition to be administered in accordance with each patient's symptoms.

The present pharmaceutical composition may include pharmaceutical agents other than the above-mentioned compounds, such as SSRIs and/or serotonin-noradrenergic reuptake inhibitors (hereinafter referred to as SNRIs).

The compounds mentioned above in this pharmaceutical composition may include a mood disorder, mental disorder, and/or a chronic fatigue syndrome therapeutic agent as the only approach to achieve treatment planning in accordance with the cause.

For example, a mood disorder, a mental disorder, and/or a chronic fatigue syndrome caused by only muscle abnormality of the inner circumscribing surface of the skull may be treated exclusively with the present pharmaceutical composition.

Conversely, a mood disorder, mental disorder, and/or the chronic fatigue syndrome of a composite cause (caused by both a muscle abnormality of an inner circumscribing surface of the skull and a serotonin deficiency) can be addressed with a flexible treatment method like a combination of the present pharmaceutical composition and an established SSRI and/or SNRI.

The amount of the compound in the present pharmaceutical composition may be altered in accordance with the structure of the selected compound, symptoms of the patient, dosage form, and amount required in one administration. For example, a general formulation amount includes the amount of the compound at 1% to 90% mass, preferably 1% to 85% mass, and more preferably 1% to 80% mass. When two or more compounds having the above-mentioned structure are contained in the present pharmaceutical composition, the total amount of these compounds may be within the range of the above-mentioned blending amount.

2. Carriers

Any of the carriers which can be employed in the production pharmaceutical compositions can be adopted without any limitation in the preparation of the present pharmaceutical composition.

These carriers include fillers, extenders, binders, wetting agents, disintegrants, surfactants, diluents such as a lubricant, and excipients, which are commonly used in pharmaceutical compositions.

These carriers can be used appropriately depending on dosage forms.

The use of specific carriers is described below for each dosage form.

3. Capable Formulation of the Present Pharmaceutical Composition

The present pharmaceutical composition can employ any formulation that can be employed in general.

For example, solid dosage for internal use by oral administration of pills, capsules, powders, and granules, ingestion liquid medicine of water agents, suspending agents, emulsions, syrups, and elixirs, and dosage forms for non-parenteral administration of ointments, gelling agents, cream agents, poultice agents, patches, sprays, inhalation agents, spray agents, and injection agents can be adopted with the present pharmaceutical composition.

4. Carriers Appropriate for Each Dosage Form

Excipients such as lactose, mannitol, glucose, non-crystalline cellulose, and starch, a binder such as hydroxypropyl cellulose, polyvinyl pyrrolidone, and magnesium metasilicate aluminate, and a disintegrant such as cellulose glycolate may be used as carriers. Lubricants such as magnesium stearate, a dissolution aid such as glutamic acid or aspartic acid, and a stabilizer may also be used. The formulation may be coated with a single or multiple layer.

In the liquid for internal use, for example, purified water, ethanol, or a mixture of both is used as a diluent.

The above diluent may optionally include a wetting agent, a suspending agent, an emulsifier, a sweetener, a flavoring agent, one or more components selected from an aromatic, a preservative, and a buffering agent.

Carriers that can be used in ointments are appropriate for use with the present pharmaceutical composition, including the following: higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), waxes (beeswax, spermaceti, ceresin, etc.), and a surfactant (polyoxyethylene alkyl ether phosphate ester, etc.), higher alcohols (cetanol, stearyl alcohol, ceetostearyl alcohol, etc.), silicone oil (dimethylpolysiloxane, etc.), hydrocarbons (hydrophilic petrolatum, white petrolatum, refined lanolin, liquid paraffin, etc.), glycols (ethylene glycol, diethylene glycol, propylene glycol, polyethylene glycol, macrogol, etc.), vegetable oil (castor oil, olive oil, sesame oil, tele-pin oil, etc.), animal oil (mik oil, yolk oil, squalane, squalene, etc.), water, an absorption promoter, an anti-shake agent, a humectant, a preservative, a stabilizer, an antioxidant, and a flavoring agent, etc.

Carriers that can be used in gel agents are appropriate for use with the present pharmaceutical composition, including the following: lower alcohols (ethanol, isopropyl alcohol, etc.), gelling agents (carboxymethyl cellulose, hydroxyethyl cellulose, hydroxypropyl cellulose, ethyl cellulose, etc.), a neutralizing agent (triethanolamine, diisopropanolamine, etc.), a surfactant (polyethylene glycol monostearate), gums, water, absorption enhancers, an anti-shake agent, a preservative, an antioxidant, and a flavoring agent, etc.

Carriers that can be used in cream agents are appropriate for use with the present pharmaceutical composition, including the following: higher fatty acid esters, lower alcohols, hydrocarbons, polyhydric alcohols (propylene glycol, 1,3-butylene glycol, etc.), higher alcohols (2-hexyldecanol, cetanol, etc.), an emulsifier (a polyoxyethylene alkyl ether, a fatty acid ester, etc.), water, an absorption promoter, an anti-shake agent, a preservative, an antioxidant, and a flavoring agent, etc.

Carriers that can be used in poultice are appropriate for use with the present pharmaceutical composition, including the following: a thickener (polyacrylic acid, polyvinyl pyrrolidone, gum arabic, starch, gelatin, methyl cellulose, etc.), a wetting agent (urea, glycerin, propylene glycol, etc.), a filler (kaolin, zinc oxide, talc, calcium, magnesium, etc.), water, a dissolution aid, tackifiers, anti-shake agents, preservatives, antioxidants, and flavoring agents, etc.

Carriers that can be used in patches are appropriate for use with the present pharmaceutical composition, including the following: a polymer base, oil, fat, higher fatty acid, tackifiers, anti-shake agents, preservatives, antioxidants, and flavoring agents, etc.

Carriers that can be used in liniment agents are appropriate for use with the present pharmaceutical composition, including the following: alcohols (ethanol, polyethylene glycol, etc.), a higher fatty acid, a glycerin, a soap, an emulsifier, a suspending agent, a preservative, an antioxidant, and a flavoring agent, etc.

Carriers used in sprays, inhalants, and sprays agents are also appropriate for use with the present pharmaceutical composition, including the following: stabilizers such as sodium hydrogen sulfite other than the diluent generally used, and a cushioning material giving isotonicity, for example, sodium chloride, sodium citrate, and citric acid, etc.

Injectable compositions for parenteral administration, solution, suspension, an emulsion, and a solid injection which is dissolved or suspended in a solvent when used, etc. are appropriate for use with the present pharmaceutical composition.

The injection is used by dissolving, suspending, or emulsifying one or more active substances in a solvent.

Examples of an appropriate solvent include distilled water for injection, physiological saline, vegetable oil, propylene glycol, polyethylene glycol, alcohols such as ethanol, and combinations of these options.

Furthermore, these injection agents may be included with a stabilizer, a dissolution aid (glutamic acid, aspartic acid, polysorbate 80 [registered trademark], etc.), a suspending agent, an emulsifier, a pain-free agent, a buffering agent, and a preservative, etc.

Appropriate inhalation agents for parenteral administration include aerosol agents, inhalation powder agents, or inhalation liquid agents.

The inhalation solution may be dissolved or suspended in water or another suitable medium during use.

For example, in the case of a liquid for inhalation, preservatives (benzalkonium chloride, paraben, etc.), coloring agents, buffering agents (sodium phosphate, sodium acetate, etc.), isotonic agents (sodium chloride, concentrated-glycerin, etc.), thickeners (carboxyvinyl polymers, etc.), and absorption promoters, etc. may be appropriately selected and prepared as needed.

In the case of inhalation powder, lubricants (stearic acid and its salts, etc.), binders (starch, dextrin, etc.), excipients (lactose, cellulose, etc.), colorants, preservatives (benzalkonium chloride, paraben, etc.), and absorption promoters, etc. may be appropriately selected and prepared as needed.

When administering an inhalation solution, a spray device (atomizer, nebulizer) is usually used. When administering an inhalation powder, an inhaler for a powder medicine is usually used.

5. Method for Producing the Present Pharmaceutical Composition

The present pharmaceutical composition can be produced by a conventional method for producing a pharmaceutical composition. For example, when a tablet is used as a dosage form, the compound is added to one of the above-mentioned carriers and mixed. A tablet of arbitrary size can be produced by compressing the obtained mixture.

6. Use of the Present Pharmaceutical Compositions for Mood Disorder, Mental Disorder, and/or Chronic Fatigue Syndrome As described above, pharmaceutical compositions of the present invention may be applied for the treatment of mood disorders, mental disorders, and/or chronic fatigue syndrome. SSRIs for the treatment of mood disorders, mental disorders, and/or chronic fatigue syndrome may be used with other therapeutic agents for mood disorders, mental disorders, and/or another chronic fatigue syndrome may be used in combination with the present pharmaceutical composition.

Dosage of the present pharmaceutical composition for treating mood disorders, mental disorders, and/or chronic fatigue syndrome may vary depending on the type and amount of the compound(s) contained in the pharmaceutical composition. Additionally, dosage will depend on the patient's age, body weight, symptoms, treatment effects, and administration methods.

The administration amount shown below is expressed as an amount per day of one adult weighing 60 kg.

The following dose is based on a one per day regimen. However, if necessary, it may be administered at once or multiple times (for example, two to six times).

The general administration amount of the compound included in the present pharmaceutical composition is as follows: 10~10000 mg, preferably 300-8000 mg, and more preferably 500-6000 mg.

When chlorphenesin carbamate is used as a compound in the present pharmaceutical composition, an appropriate amount of administration would be 10~10000 mg, preferably 300-8000 mg, and more preferably 500-6000 mg.

When a methocarbamol is used as a compound in the present pharmaceutical composition, an appropriate amount of administration would be 10~10000 mg, preferably 300-8000 mg, and more preferably 500-6000 mg.

When both chlorphenesin carbamate and methocarbamol are used as compounds in the present pharmaceutical composition, an appropriate amount of administration would be ~10000 mg, preferably 300-8000 mg, and more preferably 500-6000 mg.

In this case, an appropriate mixing ratio of the chlorphenesin carbamate to the methocarbamol would be 10:90 to 90:10, preferably 30:70 to 70:30, and more preferably 40:60 to 60:40.

The mixing ratio in the range, the degree of the therapeutic effect on the disease, and the action time can be adjusted according to the setting.

The following examples describe potential pharmaceutical compositions of the present invention in more detail. Of course, the examples do not affect the scope of the present invention.

EXAMPLE

Animal Experiments

The antidepressant action of a test substance may be evaluated using a "forced swimming method" in a mouse model.

The forced swimming test in mouse models is an animal experimental method for confirming the antidepressant activity proposed by Porsalt (Arch. Int, pharmacydn. 229.327-336 (1977)).

A mouse placed into a pool indicates either an active state or a non-moving state. Decreases in the non-moving state of the mouse is used as an index to confirm the antidepressant action of a pharmaceutical composition.

1. Pool for Forced Swimming

The pool used for forced swimming was a glass cylindrical container 30 cm in height and 16 cm in inner diameter filled at a water depth of 20 cm at 25° c.

2. Test Animal

Animal species: mouse
System: Slc: ICR
Sex: male
Supply source: Japan LSC Co. Ltd.
Microbiological grade: SPF
Age on arrival day: 8 weeks old
Age on test day: 9 weeks old
Individual identification: A label describing test number, cage number, and individual identification number was installed in the cage. An individual identification number was written on the tail of the animal.

3. Substances Used for Testing and Preparing the Pharmaceutical Composition Used in the Test Methocarbamol was used in this test of the present invention.

Etizolam was used as a comparative example with the present invention, which is commonly used as an antianxiety agent in the treatment of depression.

A 260 mg methocarbamol formulation (manufactured by Ying-Yuag chemical pharmaceutical Co. Ltd., product name bolaxin, methocarbamol content: 76% mass) was added to the distilled water until reaching a volume of 10 mL, and 200 mg of the distilled water/10 ml of a methocarbamol aqueous solution (2% mass in terms of methocarbamol) was prepared (reagent name M-1).

A 3.3 mg etizolam formulation (trade name etilaam-1, etizolam content: 0.01 mass %, produced by INTAS PHARMACEUTICAL Co. Ltd.) was also added to the distilled water until reaching a volume of 10 mL, and 0.033 mg of the distilled water/10 ml of etizolam aqueous solution (0.00033% mass in terms of etizolam) was prepared (reagent name E-1). Table 1 below shows the dose for each mouse.

TABLE 1

|  | Ingredient name | Dosage amount |
| --- | --- | --- |
| Example (Reagent M-1 administration group) | Methocarbamol | 200 mg/kg |
| Comparative example (Reagent E-1 administration group) | Etizolam | 0.033 mg/kg |

4. Forced Swimming Test (1) Embodiment 1

One hour before the test, 10 mL/kg of the above prepared methocarbamol aqueous solution was administered to the mouse only once (200 mg/kg in methocarbamol conversion).

The administration route was a forced oral administration using an installed mice oral administration sonde made by FUCHIGAMI with a syringe for injection made by TERUMO.

The method was carried out under non-anesthesia.

After one hour of forced administration, the mouse was placed in the forced swimming pool described above and left for 10 minutes.

The first three minutes after entering were considered a conditioning period, and the mouse's non-moving time in the remaining 7 minutes was measured.

"Non-motion" was defined by the mouse not moving the anterior limb and the posterior limb, and by a state in which the upper side of the neck is lifted from the water surface and floats.

The "non-moving time" was the sum of "non-motion" time.

The test was repeated 10 times for each mouse, and an average value was calculated.

(2) Comparative Example

An etizolam aqueous solution was used in place of a methocarbamol aqueous solution. The same test as described above (1) was performed, but with the administration amount converted to etizolam usage at 0.0333 mg/kg.

(3) Medium Control

Distilled water not containing a pharmaceutical was used in place of the methocarbamol aqueous solution in the same manner as described above (1).

5. Results

The average non-moving time values of the medium control group (n=10), the examples, and comparative examples (n=10) were compared with each other.

Table 2 below shows the average values.

TABLE 2

| Administration group | Immobile time average value (sec) | standard deviation |
|---|---|---|
| Medium handling group | 230.8 | 17 |
| Example (Reagent M-1 administration group) | 157.7 | 20.1 |
| Comparative example (Reagent E-1 administration group) | 107.3 | 18.5 |

The "non-moving time" was 230.8 seconds in the medium control group, 107.3 seconds in the etizolam control group, and 157.7 seconds in the methocarbamol dose group. Thus, it is apparent that the methocarbamol administration group had essentially the same effect as the etizolam administration group.

Test for administration to depression patients (embodiment 1)

1. Treatment of Depression Patients

Preparation of pharmaceutical compositions comprising (1) methocarbamol

A 500 mg bolaxin tablet (manufactured by Ying-Yuan chemical pharmaceutical co. ltd.) and 500 mg-containing (methocarbamol content 76% mass) were prepared.

2. Patient

A subject suffering from depression for two or more years was selected.

3. Treatment Method

A pharmaceutical composition was administered to the patient three times a day, and the administration was continued for one week.

The dose on the initial day was 3.0 to 4.5 g/day (converted to methocarbamol).

After observing the patient's state, it was increased to 6.0 g/day (converted to methocarbamol).

(all doses were recorded).

The regular drug in addition to the tested pharmaceutical composition was continuously taken, but drinking was prohibited during the test.

4. Judgment of Results

After one week, a potential depression improvement effect before and after administration was evaluated.

The evaluation investigated a significant difference in two-term judgment of two related groups.

The evaluation was judged based on a declaration of whether the subjects felt an improvement in thinking, desires, and fatigue.

5. Results

Table 3 below shows the test results after one week.

TABLE 3

| N number | 5 persons |
|---|---|
| Effective | 5 persons |
| No effect | 0 persons |

As described above, it was confirmed that a pharmaceutical composition containing methocarbamol had a beneficial depression treatment effect.

INDUSTRIAL APPLICABILITY

The present invention provides an alternative pharmaceutical composition for patients who have not been treated with SSRIs or similar drugs, patients who are resistant to the beneficial effects of SSRIs. This invention aims to decrease side effects relative to treatment with SSRIs and provide a method for more effective treatment and/or prevention of mood disorders, mental disorders, and/or chronic fatigue syndrome.

The invention claimed is:

1. A method of treating depression, and/or chronic fatigue syndrome, comprising administering to a subject in need thereof a pharmaceutical composition containing one or more kinds of compounds of the following structure:

[formula 1]

$$H_2N-C(=O)-O-CH_2-CH(OH)-CH_2-O-C_6H_4-R$$

wherein R is an alkyloxy group containing 1 to 3 carbon atoms or a halogen group.

2. The method according to claim 1, wherein R is a methoxy group or a chloro group.

3. The method according to claim 1, wherein the compound is chlorphenesin carbamate and/or methocarbamol.

4. The method according to claim 1, wherein the pharmaceutical composition includes both chlorphenesin carbamate and methocarbamol.

* * * * *